US008685949B2

(12) United States Patent
Chung et al.

(10) Patent No.: US 8,685,949 B2
(45) Date of Patent: Apr. 1, 2014

(54) USE OF 25-HYDROXY VITAMIN $D_3$ TO IMPROVE VITALITY OF ANIMALS

(75) Inventors: Thau Kiong Chung, Singapore (SG); Francisco Feranil Penalba, Laguna (PH); Gilbert Weber, Magden (CH)

(73) Assignee: DSM IP Assets B.V., Heerlen (NL)

( * ) Notice: Subject to any disclaimer, the term of this patent is extended or adjusted under 35 U.S.C. 154(b) by 798 days.

(21) Appl. No.: 12/094,878

(22) PCT Filed: Nov. 23, 2006

(86) PCT No.: PCT/EP2006/011236
§ 371 (c)(1),
(2), (4) Date: Oct. 14, 2008

(87) PCT Pub. No.: WO2007/059960
PCT Pub. Date: May 31, 2007

(65) Prior Publication Data
US 2009/0221537 A1      Sep. 3, 2009

(30) Foreign Application Priority Data

Nov. 25, 2005  (EP) .................................... 05025723
Mar. 17, 2006  (EP) .................................... 06005440

(51) Int. Cl.
*A61K 31/59*     (2006.01)
*A61P 39/00*     (2006.01)

(52) U.S. Cl.
USPC ....................................................... 514/167

(58) Field of Classification Search
USPC ....................................................... 514/167
See application file for complete search history.

(56) References Cited

U.S. PATENT DOCUMENTS

| 4,970,203 A * | 11/1990 | Deluca et al. ............... 514/167 |
| 7,632,518 B2 * | 12/2009 | Tritsch et al. ............... 424/442 |
| 2002/0198185 A1 | 12/2002 | Real et al. |
| 2003/0050341 A1 * | 3/2003 | Bydlon et al. ............... 514/560 |

FOREIGN PATENT DOCUMENTS

| EP | 1 529 445 | 5/2005 |
| JP | 2005-192514 | 7/2005 |
| RU | 2 096 969 | 11/1997 |

OTHER PUBLICATIONS

Soares, J. H. et al., "25-Hydroxycholecalciferol in Poultry Nutrition", Poultry Science, vol. 74, No. 12, pp. 1919-1934, (1995).
Atencio A. et al., "Twenty-Five Hydroxycholecalciferol as a Substitute in Broiler Breeder Hen Diets and its Effect on the Performance and General Health of the Progeny", Poultry Science, vol. 84, No. 8, pp. 1277-1285, (Aug. 2005).
International Search Report for PCT/EP2006/011236, mailed Mar. 22, 2007.
Written Opinion of the International Searching Authority, mailed Mar. 22, 2007.

* cited by examiner

*Primary Examiner* — San-Ming Hui
*Assistant Examiner* — Kathrien Cruz
(74) *Attorney, Agent, or Firm* — Nixon & Vanderhye P.C.

(57) ABSTRACT

The present invention relates to the use of 25-hydroxy-vitamin $D_3$ to improve the general health status of female animals at least during gestation and/or lactation. The invention also relates to the use of 25-hydroxy-vitamin $D_3$ in animal breeding. More particular, the invention relates to the use of 25-hydroxy-vitamin $D_3$ for improving litter size and vitality of piglets in pig breeding and for providing better body frame and increasing gestation backfat gain, reducing lactation backfat loss and increasing lactation feed intake of sows and gilts.

9 Claims, No Drawings

USE OF 25-HYDROXY VITAMIN D$_3$ TO IMPROVE VITALITY OF ANIMALS

This application is the U.S national phase of International Application No. PCT/EP2006/011236, filed on 23 Nov. 2006, which designated the U.S. and claims priorty to European Application No. 05025723.7, filed 25 Nov. 2005, and European Application No. 06005440.0 filed 17 Mar. 2006, the entire contents of each of which are hereby incorporated by reference.

The present invention relates to the use of 25-hydroxy-vitamin D$_3$ to improve the general health status of female animals during gestation and/or lactation.

The present invention also relates to the use of 25-hydroxy-vitamin D$_3$ in animal breeding. More particular, the invention relates to the use of 25-hydroxy-vitamin D$_3$ for improving litter size and vitality of piglets in pig breeding and for providing better body frame and increasing gestation backfat gain, reducing lactation backfat loss and increasing lactation feed intake of sows and gilts.

The main aim of breeding sows is to produce the maximum number of pigs weaned per sow per year at the lowest cost. Any slight improvement in the sow productivity will have a major significant positive impact on the reproductive performance of the entire breeding herd and on the overall profitability of the swine enterprise. For example, a mere increase of 0.2 pigs weaned per sow per year translates into an extra 200 market pigs in a 1000-sow farrow-to-finish operation.

It is well accepted that a wide variation of sow productivity in swine breeding herds exists within and among countries and regions. From low to high productive herds, litter size of pigs born alive ranges from 7 to 13 and litter size of pigs weaned from 5 to 12. Therefore, there is a considerable potential for improving sow productivity.

Reproductive efficiency is greatly influenced by the highly variable loss of potential piglets during the course of gestation. Fifteen to 20% of fetuses are lost between day 30 and 50 of gestation and an additional 5 to 10% loss occurs from day 90 to 114. The losses in the early part of gestation may be precipitated by factors influencing implantation (interaction between embryo and uterus), whereas those in the latter part of gestation is restricted to the available uterine space per piglet, which is more likely to be a limiting factor in younger sows.

Litter size is the key parameter affecting the number of pigs born alive and weaned per sow per year. Genetic improvements, novel gilt management and modern production management techniques are practical approaches that are employed to increase litter size and breeding herd productivity. From the standpoint of reproductive physiology, a rational approach to increasing litter size in pigs must be commensurate with successful implantation and sustainable pregnancy and an increase in uterine capacity via the increase in uterine horn length during the course of gestation. In addition, sows producing bigger litter sizes must have good milking characteristics to be capable of rearing extra pigs and supporting them nutritionally for health and growth during the course of lactation so that the increase in the number of pigs weaned per litter can be realized.

In accordance with the present invention it has been found that administering 25-hydroxy-vitamin D$_3$ to female animals, for example sows and gilts, improves litter size of piglets born alive and of piglets weaned and thus improves vitality of piglets produced from so-fed pregnant gilts and sows. Vitality is reflected in the improvement of litter size by an increase in the number of piglets born alive and in the number of weaned piglets. In another aspect, the use of 25-hydroxy-vitamin D$_3$ results in the production of healthier piglets which survive better than those from sows fed without 25-hydroxy-vitamin D$_3$ as evidenced by a reduced piglet mortality during lactation. It has been found also, that administering 25-hydroxy-vitamin D$_3$ to sows and gilts, respectively, provides better body frame and increases gestation backfat gain, reduces lactation backfat loss and increases lactation feed intake of sows and gilts.

Thus, in one aspect, the invention relates to the use of 25-hydroxy-vitamin D$_3$ for improving litter size in animal breeding, for example in pig breeding. In another aspect the invention relates to the use of 25-hydroxy-vitamin D$_3$ for improving vitality of young animals, for example piglets, by administering an effective amount of 25-hydroxy-vitamin D$_3$ to sows and gilts.

In another aspect, the invention relates to the use of 25-hydroxy-vitamin D$_3$ for improving the general health status of female animals at least during gestation and/or lactation, which means providing better body frame and/or increasing gestation backfat gain, and/or reducing lactation backfat loss and/or increasing lactation feed intake of female animals.

In still another aspect the invention relates to a method of improving litter size and vitality of young animal, for example piglets, in animal breeding which comprises administering sows and gilts an effective amount of 25-hydroxy-vitamin D$_3$.

In yet another aspect, the invention relates to a method of providing better body frame and increasing gestation backfat gain, reducing lactation backfat loss and increasing lactation feed intake in female and young animals, for example sows and gilts, which comprises administering such animals an effective amount of 25-hydroxy-vitamin D$_3$.

In the framework of the invention, with animals is meant animals, including mammals, examples of which include humans. Preferred examples of mammals beside humans are ruminant and non-ruminant animals, for example cattle, pets as dogs and cats, horses, camels, sheep, goats and pigs.

The term "sows" as used herein comprises gilts, i.e., female pigs that are intended to become fertilized and have never been conceived or serviced by the boar; as well as parity-one sows, which can also be referred to as primiparous sows; and multiparous sows, i.e. sows that have given birth to more than one litter.

The term "better body frame" denotes an increase of the number of gilts meeting the body condition standard after performance testing and evaluation as measured by the scoring system for evaluating feet and leg structure according to the "Guidelines for Uniform Swine Improvement Programs" (National Swine Improvement Federation, NSIF, 1996), the evaluation of "Feet and Leg Soundness in Swine" (Pork Industry Handbook, PIH 101) and the evaluation of toe sizes and hooves As used herein, the term food product refers to any food or feed suitable for consumption by humans or animals. The food product may be a prepared and packaged human food or food supplement or an animal feed (e.g., extruded and pelleted animal feed, coarse mixed feed or pet food composition). The term food comprises also both solid and liquid food as well as drinking fluids such as drinking water.

For the consumption by human in order to improve the general health status of a mother during gestation and/or lactation, a food supplement according to the invention may be administered in the form of unit dosages, for example tablets, capsules, measured powders, or measured liquid portions, which may, if desired, be carbonated. Furthermore, the food supplements of the invention may additionally contain conventional inert and physiologically acceptable carriers, flavouring agents, colouring agents and calcium. For example a tablet may be supplemented with 25-hydroxy vitamin $D_3$ in an amount to satisfy a daily dosage of 25-hydroxy vitamin $D_3$ from about 5 to 15 mcg per kg body weight, wherein the usual daily dose is 1 or 2 tablets.

In the following the invention is described in more detail with regard to animal breeding.

For the purposes of the invention, 25-hydroxy-vitamin $D_3$ is suitably administered as supplement to food. Food may be supplemented by admixing 25-hydroxy-vitamin $D_3$, e.g., as a commercial formulation such as available under the Trademark ROVIMIX® Hy•D® 1.25% to regular food or by first preparing a premix of a food component and 25-hydroxy-vitamin $D_3$ and subsequent mixing the premix with other food components. The food can be any conventional pig food. The term food as used herein comprises both solid and liquid food as well as drinking fluids such as drinking water. Particularly, 25-hydroxy-vitamin $D_3$ can be added as a formulated powder to a premix containing other minerals, vitamins, amino acids and trace elements which premix is added to regular animal food and thorough mixing to achieve even distribution therein.

For the purposes of the invention, 25-hydroxy-vitamin $D_3$ is administered in at least one stage of the reproductive cycle (gestation and lactation) and is suitably administered also in replacement gilt development, i.e. development of female pigs selected to replace culled sows in the breeding herd.

Generally, 25-hydroxy-vitamin $D_3$ is added to sow food in an amount required to administer from about 0.1 mcg to about 3.0 mcg, especially about 0.5 mcg to about 2.0 mcg of 25-hydroxy-vitamin $D_3$ per kg body weight of an individual animal per day.

More specifically, in the manufacture of a gilt/sow food in accordance with the invention, from about 10 mcg/kg to about 100 mcg/kg of 25-hydroxy-vitamin $D_3$ are suitably added to regular pig food. Alternatively, a food premix may be prepared on the basis of regular food components by adding active ingredients to such food components in higher concentration, e.g., in a concentration of from about 10 mg/kg to about 100 mg/kg of 25-hydroxy-vitamin $D_3$. If one kg of such premix is added per 1000 kg of regular food this would typically meet the individual need of the animal by normal food consumption.

Based on the requirements of the individual gilt and gestating sow, 25-hydroxy-vitamin $D_3$ is suitably administered for the purposes of the invention in amounts from about 0.125 mcg to about 1.250 mcg, especially about 0.625 mcg to about 1.000 mcg per kg body weight per day. Thus, 25-hydroxy-vitamin $D_3$ is suitably added to the food in an amount to satisfy such dosage requirement. Typically, a gilt and gestating sow food may contain from about 10 mcg to about 100 mcg, especially of from about 50 mcg to about 80 mcg 25-hydroxy-vitamin $D_3$ per kg food.

Furthermore, based on the requirements of the individual lactating sow, 25-hydroxy-vitamin $D_3$ is suitably administered for the purposes of the invention in amounts from about 0.250 mcg to about 2.500 mcg, especially about 1.250 mcg to about 2.000 mcg per kg body weight per day. Thus, 25-hydroxy-vitamin $D_3$ is suitably added to the food in an amount to satisfy such dosage requirement. Typically, a lactating sow food may contain from about 10 mcg to about 100 mcg, especially of from about 50 mcg to about 80 mcg 25-hydroxy-vitamin $D_3$ per kg food.

For calculating the body weight and feed intake of gilts and gestating sows an average of 200 kg body weight and 2.5 kg feed per day may be taken. For calculating the body weight and feed intake of lactating sows an average of 200 kg body weight and 5 kg feed per day may be taken.

The efficiency of the treatment of gilts in accordance with the invention can be seen from the two experiments described below.

EXPERIMENT 1

In a commercial pig farm a total of 27 six-month-old replacement gilts (Landrace×Large White) were selected. There were two dietary treatments in different stages of the reproductive cycle (replacement gilt development, gestation, lactation). The control diet was the standard farm diet without the supplementation of 25-hydroxy-vitamin $D_3$. The experimental diet was the standard farm diet supplemented with 25-hydroxy-vitamin $D_3$ at 50 mcg per kg diet.

Fourteen (14) gilts were randomly selected and assigned to the control group and the other 13 gilts to the ROVIMIX® Hy•D® 1.25% group. Breeding started when the gilts were 7 months old. They were placed in the gestating stalls after breeding and remained there until 14 days before the expected date of farrowing. They were then weighed and moved to the farrowing stalls. Piglets were weaned at 28 days of age.

EXPERIMENT 2

In another commercial pig farm a total of 43 six-month-old replacement gilts (Landrace×Large White) were selected. There were two dietary treatments in different stages of the reproductive cycle (replacement gilt development, gestation, lactation). The control diet was the standard farm diet without the supplementation of 25-hydroxy-vitamin $D_3$. The experimental diet was the standard farm diet supplemented with 25-hydroxy-vitamin $D_3$ at 50 mcg per kg diet.

Twenty-two (22) gilts were randomly selected and assigned to the control group and the other 21 gilts to the ROVIMIX® Hy•D® 1.25% group. Breeding started when the gilts were 7 months old. They were placed in the gestating stalls after breeding and remained there until 14 days before the expected date of farrowing. They were then weighed and moved to the farrowing stalls. Piglets were weaned at 28 days of age.

The following data were collected in the farrowing stalls in Experiments 1 and 2:
1. Litter size at birth
   a. Total pigs born
   b. Pigs born alive
   c. Stillborn pigs
   d. Mummified fetuses
2. Pig weight at birth
3. Litter size at weaning
4. Mortality
5. Pig weight at weaning Table 1 (Experiment 1) shows that reproductive performance of parity-one sows fed 25-hydroxy-vitamin $D_3$ had larger litter size at birth both in terms of total pigs born (10.46 vs. 9.00; +1.46) and pigs born alive (9.77 vs. 7.93; +1.84) than those gilts that were fed ration without supplemental 25-hydroxy-vitamin $D_3$ (Control). Litter size at weaning was also larger for the 25-hydroxy-vitamin $D_3$-treated group than for the control group (9.46 vs. 7.64+1.82). The control group, however, had a heavier birth weight (1.64 vs. 1.45 kg). Weaning weights were not different from each other. However, piglets from gilts fed 25-hydroxy-vitamin $D_3$ gained 5.5 kg versus 5.33 kg for those from gilts in the control group at 28-day weaning.

TABLE 1

Reproductive performance of parity-one sows
fed 25-hydroxy-vitamin $D_3$ (Experiment 1)

| Treatment | Number of sows | LSBT | LSBA | BWT, kg | LSW | WWT, kg |
|---|---|---|---|---|---|---|
| Control | 14 | 9.00 | 7.93 | 1.64 | 7.64 | 6.97 |
| ROVIMIX ®Hy•D ®1.25% | 13 | 10.46 | 9.77 | 1.45 | 9.46 | 6.95 |

LSBT = Litter size of total number of pigs at birth; LSBA = Litter size of number of pigs born alive; BWT = Body weight of pigs at birth; LSW = Litter size of number of pigs weaned at 28-day weaning; WWT = 28-day weaning body weight.

TABLE 2

Reproductive performance of parity-one sows
fed 25-hydroxy-vitamin $D_3$ (Experiment 2)

| Treatment | Number of sows | LSBT | LSBA | BWT, kg | LSW | WWT, kg |
|---|---|---|---|---|---|---|
| Control | 22 | 10.59 | 9.18 | 1.51 | 7.82 | 7.84 |
| ROVIMIX ®Hy•D ®1.25% | 21 | 10.43 | 9.62 | 1.44 | 8.48 | 7.50 |

LSBT = Litter size of total number of pigs at birth; LSBA = Litter size of number of pigs born alive; BWT = Body weight of pigs at birth; LSW = Litter size of number of pigs weaned at 28-day weaning; WWT = 28-day weaning body weight.

Table 2 (Experiment 2) shows that reproductive performance of parity-one sows fed 25-hydroxy-vitamin $D_3$ had larger litter size of pigs born alive (9.62 vs. 9.18; +0.44) than those fed a ration without supplemental 25-hydroxy-vitamin $D_3$ (Control). Litter size at weaning was also larger for the 25-hydroxy-vitamin $D_3$-treated group than for the control group (8.48 vs. 7.82+0.66).

The invention is further illustrated by the Examples which follow.

EXAMPLE 1

A food comprising the components shown in Table 3 below is supplemented with 50 to 80 mcg 25-hydroxy-vitamin $D_3$ per kg of food.

TABLE 3

| Ingredients | Replacement gilt diet, kg/1000 kg | Gestating sow diet, kg/10000 kg | Lactating sow diet, kg/1000 kg |
|---|---|---|---|
| Yellow corn | 398.12 | 432.17 | 404.47 |
| Soybean meal (Argentina) | 110.00 | 108.10 | 151.20 |
| Crude coco oil | 0.00 | 0.00 | 10.20 |
| Rice bran | 250.00 | 250.00 | 220.00 |
| Copra meal | 150.00 | 150.00 | 150.00 |
| Molasses | 50.00 | 14.00 | 20.00 |
| Monodicalcium Phosphate | 16.50 | 21.50 | 21.50 |
| Limestone | 15.20 | 13.80 | 13.20 |
| L-lysine | 2.10 | 2.00 | 2.20 |
| Choline Cl | 1.00 | 1.00 | 1.00 |
| Toxin binder | 1.00 | 1.00 | 1.00 |
| Trace mineral premix *) | 0.80 | 1.00 | 1.00 |
| Salt | 5.00 | 5.00 | 5.00 |
| Vitamin premix **) | 0.15 | 0.30 | 0.30 |
| Antioxidant | 0.13 | 0.13 | 0.13 |

| **) Composition of vitamin premix | IU or mg/kg of vitamin premix |
|---|---|
| Vitamin A | 50,000,000 |
| Vitamin D3 | 9,000,000 |
| Vitamin E | 200,000 |
| Vitamin K3 | 9,000 |
| Vitamin B1 | 9,000 |
| Vitamin B2 | 22,000 |
| Vitamin B6 | 14,000 |

TABLE 3-continued

| Vitamin B12 | 100 |
|---|---|
| Niacin | 150,000 |
| Pantothenic acid | 70,000 |
| Biotin | 1,000 |
| Folic acid | 10,000 |

| *) Composition of trace mineral premix | Mg/kg of trace mineral premix |
|---|---|
| Iron | 125,000 |
| Copper | 7,500 |
| Manganese | 25,000 |
| Zinc | 125,000 |
| Cobalt | 500 |
| Iodine | 175 |
| Selenium | 300 |

A food as specified above is supplemented with 25-hydroxy-vitamin $D_3$ by mixing 50 to 80 mg of 25-hydroxy-vitamin $D_3$ (4 to 6.4 g of ROVIMIX® Hy•D® 1.25% as supplied by DSM Nutritional Products, Kaiseraugst, Switzerland) together with the remaining food items. The obtained mash food, if needed, can be pelleted.

EXAMPLE 2

A food is prepared as indicated in Example 1 except that about 50 to 80 mg of 25-hydroxy-vitamin $D_3$ are added per kg of vitamin and mineral premix.

EXAMPLE 3

A food premix for a gilt or sow food containing 25-hydroxy-vitamin $D_3$ can be prepared as follows:

| Ingredients | [%] |
|---|---|
| ROVIMIX ® Hy•D ® 1.25% | 0.0800 |
| Vitamin A 500 | 0.8000 |
| Vitamin E 50% | 8.0000 |
| Vitamin D3 500 | 0.0800 |
| Vitamin K3 100% MSB/51% | 0.0800 |

-continued

| Ingredients | [%] |
|---|---|
| Vitamin B1 98% | 0.0714 |
| Vitamin B2 80% | 0.1750 |
| Vitamin B6 99% | 0.1212 |
| Vitamin B12 0.1% | 1.0000 |
| Biotin 2% | 0.2000 |
| Folic Acid 80% | 0.0227 |
| Niacin 99.5% | 0.7035 |
| Calpan 98% | 0.4082 |
| Vitamin C | 4.0000 |
| Choline chloride 60% | 12.0000 |
| Copper sulfate 25% | 12.8000 |
| Iron sulfate 30% | 10.0000 |
| Manganese oxide 62% | 1.6129 |
| Zinc oxide 76% | 5.2632 |
| Cobalt carbonate 5% | 0.0600 |
| Calcium iodate 62% | 0.0323 |
| Sodium selenite 1%/BMP | 0.8001 |
| BHT 100% | 2.0000 |
| Carrier Combination | 6.0000 |
| LACANTES S36400-Z | 10.0000 |
| Limestone | 23.6895 |

All ingredients are carefully mixed together and 0.5% (5 kg/1000 kg of food) of this premix is added to a conventional sow or gilt food.

Alternatively, 25-hydroxy-vitamin $D_3$ can also be added in a 1% diluted premix, containing a suitable carrier. Such carrier can be wheat flour, wheat middlings, corn cobs, rice hulls, almond shells or calcium carbonate alone or in variable mixtures of several of these carriers. A typical formula is:

| Ingredients | [%] |
|---|---|
| Rice hulls | 64.20 |
| Calcium carbonate | 35.00 |
| ROVIMIX ® Hy•D ® 1.25% | 0.80 |

All ingredients are carefully mixed together and 0.05% (0.5 kg/1000 kg of food) of this premix is added to a conventional sow or gilt food, thus providing 50 mcg 25-hydroxy-vitamin $D_3$ per kg food.

The invention claimed is:

1. A method for improving litter size and vitality of piglets in pig breeding and for providing better body frame and increasing gestation backfat gain, reducing lactation backfat loss and increasing lactation feed intake of sows and gilts; which comprises administering to a sow or gilt consuming a diet comprising Vitamin $D_3$ an effective amount of 25-hydroxy-vitamin $D_3$.

2. A method for improving litter size and vitality of piglets in pig breeding which comprises administering to a sow or gilt consuming a diet comprising Vitamin $D_3$ an effective amount of 25-hydroxy-vitamin $D_3$.

3. The method as in claim 1 wherein 25-hydroxy-vitamin $D_3$ is administered in an amount of from about 0.1 mcg to about 3.0 mcg per kg body weight per day.

4. The method as in claim 1 wherein 25-hydroxy-vitamin $D_3$ is administered as food supplement.

5. The method as in claim 4 wherein the food contains 25-hydroxy-vitamin $D_3$ in an amount of about 10 mcg to about 100 mcg per kg food.

6. The method as in claim 2 wherein 25-hydroxy-vitamin $D_3$ is administered to a gilt or gestating sow.

7. The method as in claim 2 wherein 25-hydroxy-vitamin $D_3$ is administered to a lactating sow.

8. The method as in claim 3 wherein 25-hydroxy-vitamin $D_3$ is administered in an amount of from about 0.5 mcg to about 2.0 mcg per kg body weight per day.

9. The method as in claim 5 wherein the food contains 25-hydroxy-vitamin $D_3$ in an amount of from about 50 mcg to about 80 mcg per kg food.

* * * * *